United States Patent [19]
Flower

[11] Patent Number: 5,693,024
[45] Date of Patent: Dec. 2, 1997

[54] IONTOPHORETIC DRUG DELIVERY SYSTEM, INCLUDING METHOD FOR DETERMINING HYDRATION OF PATCH

[75] Inventor: Ronald J. Flower, Vernon, N.J.

[73] Assignee: Becton Dickinson and Company, Franklin Lakes, N.J.

[21] Appl. No.: 720,125

[22] Filed: Sep. 27, 1996

[51] Int. Cl.[6] .................................................. A61N 1/30
[52] U.S. Cl. .......................................... 604/20; 607/153
[58] Field of Search ........................ 604/20, 21; 607/153

[56] References Cited

U.S. PATENT DOCUMENTS

| | | | |
|---|---|---|---|
| 4,717,378 | 1/1988 | Perrault et al. | 607/153 |
| 4,752,285 | 6/1988 | Petelenz et al. | 604/20 |
| 5,160,316 | 11/1992 | Henley | 604/20 |

Primary Examiner—Mark Bockelman
Assistant Examiner—Ellen Tao
Attorney, Agent, or Firm—Allen W. Wark

[57] ABSTRACT

An iontophoretic drug delivery system including a patch and a controller. The controller and patch include electronics which ensure proper hydration of the patch. If the controller determines that the patch is sufficiently hydrated, the controller applies current to the patch for delivery of the drug through the skin of the patient.

10 Claims, 11 Drawing Sheets

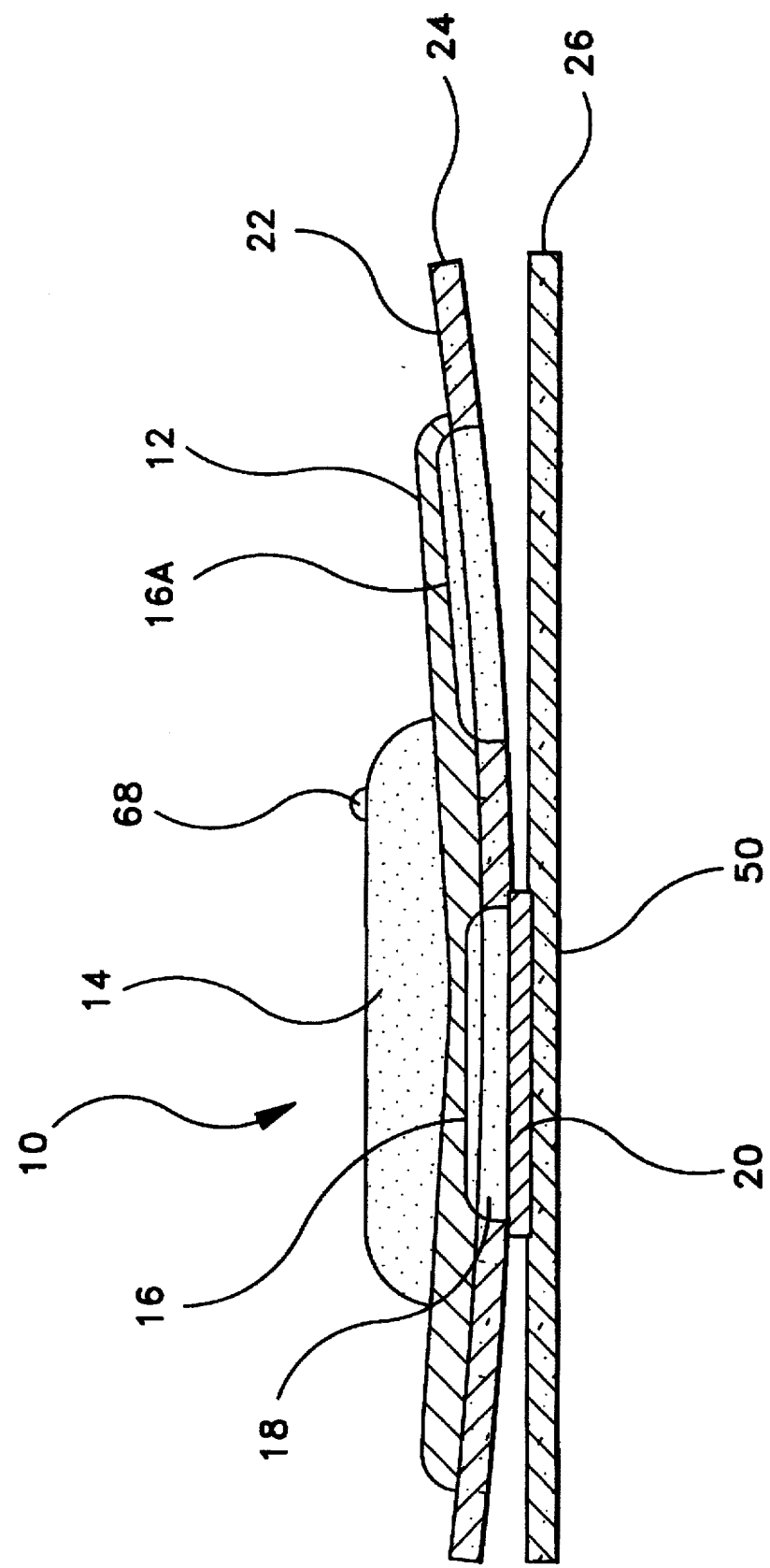

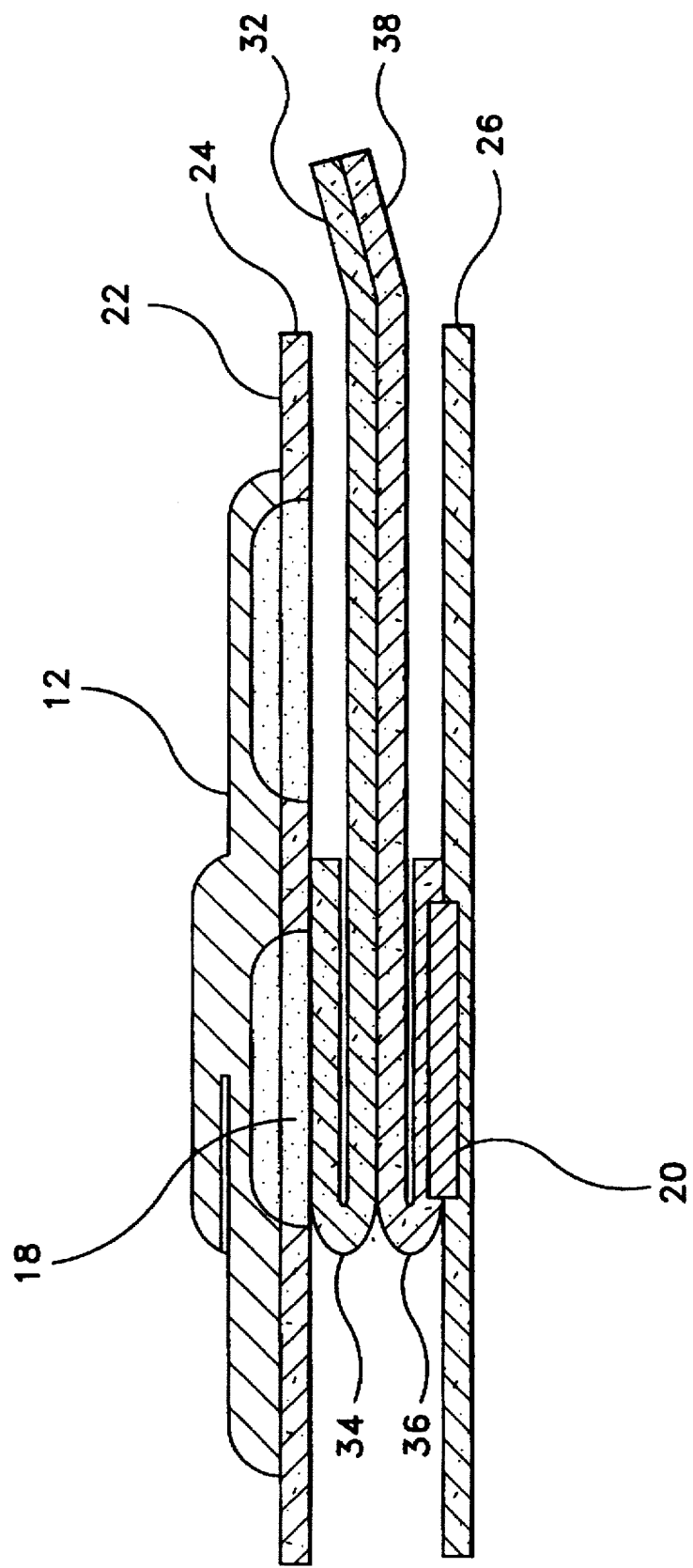

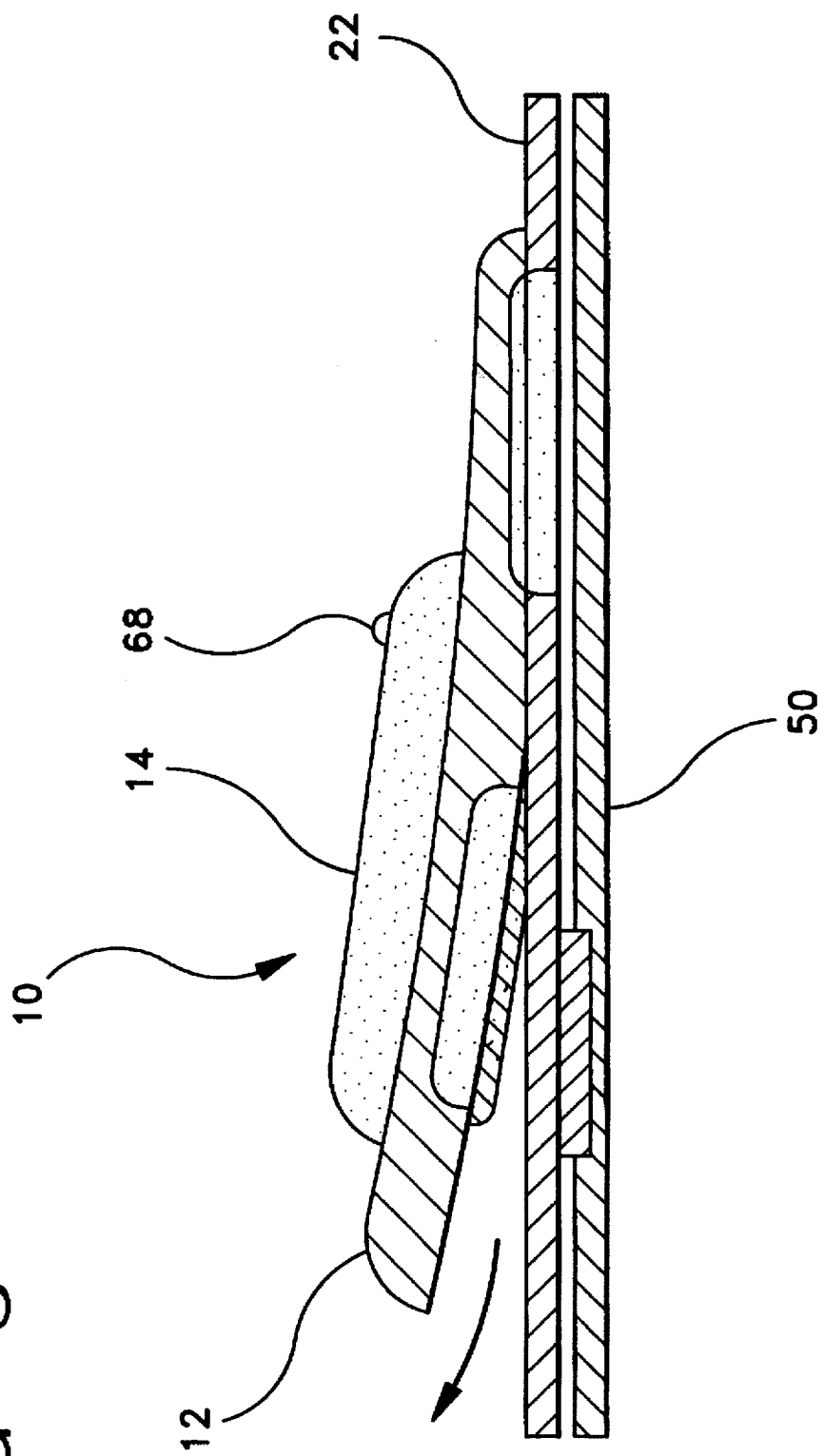

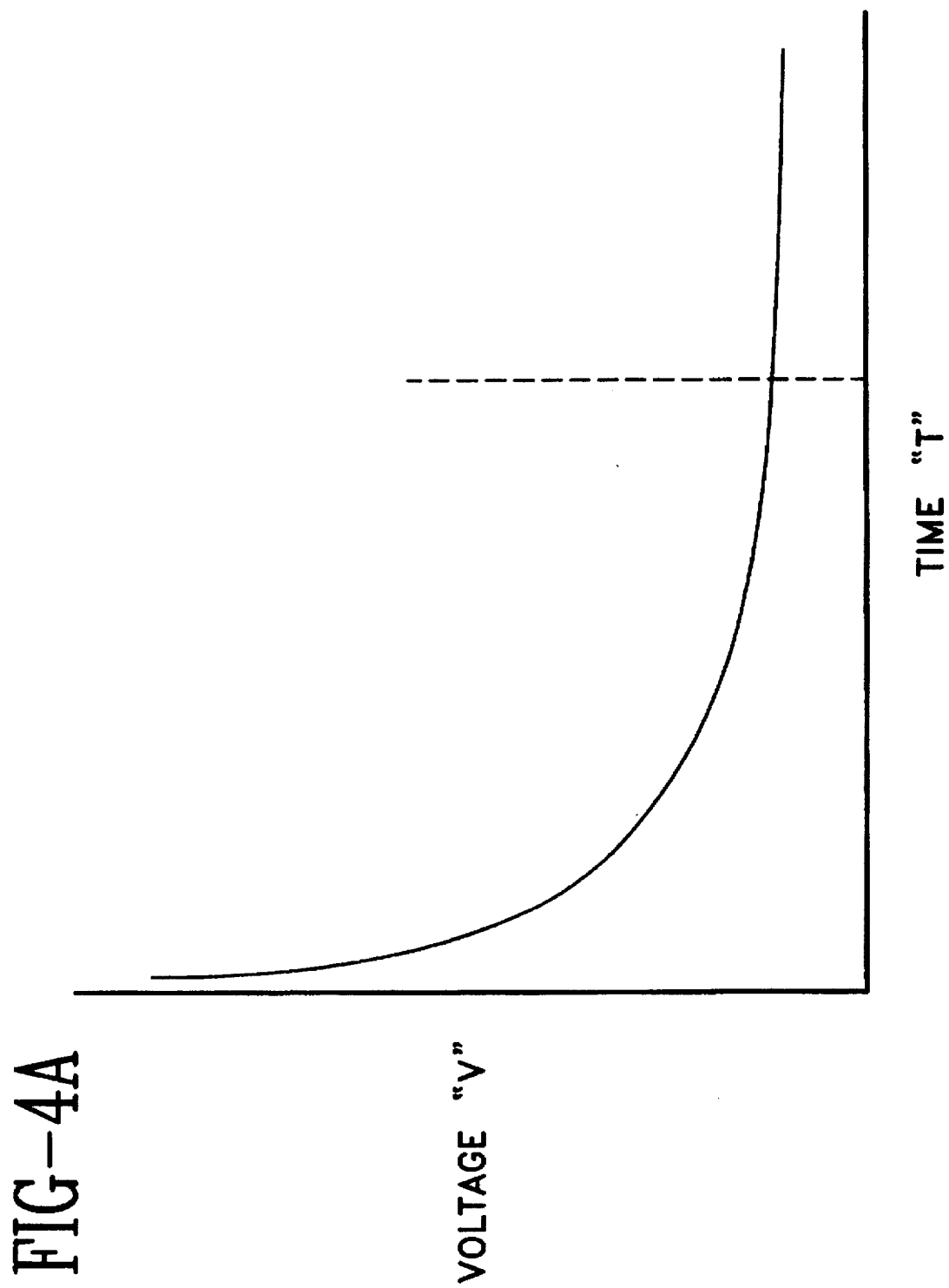

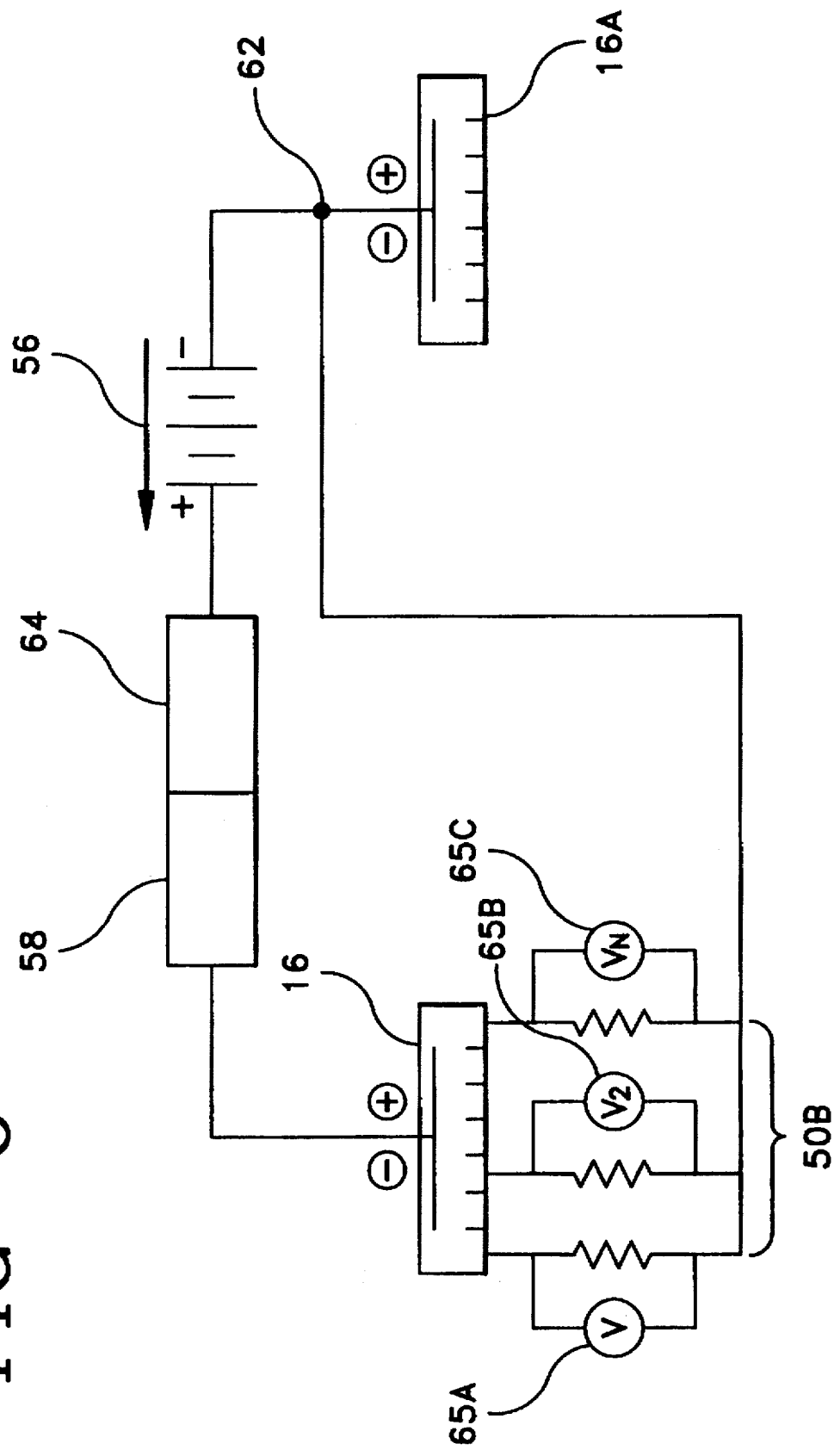

IONTOPHORETIC DRUG DELIVERY SYSTEM, INCLUDING METHOD FOR DETERMINING HYDRATION OF PATCH

Field of the Invention

The present invention generally relates to iontophoretic drug delivery systems for delivering drugs, medicines, medicaments and the like to patients transdermally, i.e., through the skin, and more specifically relates to a iontophoretic drug delivery system and method for determining hydration of disposable patch.

BACKGROUND OF THE INVENTION

Transdermal drug delivery systems have, in recent years, become an increasingly important means of administering drugs and like therapeutic agents.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using, for example, iontophoresis, which according to Stedman's Medical Dictionary, is defined as "the introduction into the tissues, by means of an electric current, of the ions of a chosen medicament." Such systems offer advantages clearly not achievable by any other methods of administration, such as avoiding introduction of the drug through the gastrointestinal tract or punctures in the skin to name a few.

Conventional iontophoretic devices, such as those described in U.S. Pat. Nos. 4,820,263 (Spevak et al.), 4,927,408 (Haak et al.) and 5,084,008 (Phipps), the disclosures of which are hereby incorporated by reference, for delivering a drug or medicine transdermally through iontophoresis, basically consist of two electrodes, which are in contact with a portion of a patient's body. A first electrode, generally called the active electrode, delivers the ionic substance or drug into the body by iontophoresis. The second electrode, generally called the counter electrode, closes an electrical circuit that includes the first electrode and the patient's body. Generally, the circuit includes a source of electrical energy, such as a battery. The ionic substance to be driven into the body may be either positively charged or negatively charged. In the case of a positively charged ionic substance, the anode of the iontophoretic device becomes the active electrode and the cathode serves as the counter electrode to complete the circuit. Alternatively, if the ionic substance to be iontophoretically delivered is negatively charged, the cathode will be the active electrode and the anode will be the counter electrode.

In practice, this process is typically achieved by placing the ionic drug either in solution or in gel form on a carrier and placing the drug-containing carrier, for example, in the form of a drug-filled adhesive patch, into contact with the skin. The pair of electrodes is placed in contact with the skin and with the carrier. Direct current is applied between the two electrodes. Under the influence of the electric field present, the drug molecules migrate through the skin. As current flows between the two electrodes placed at spaced apart locations on the skin, the current path carries the drug with it.

However, with the increasing use of drugs, particularly peptides, peptidomimetics and the like, several disadvantages and limitations have been associated with the use of such devices for delivering such drugs, including storage stability as a result of the drug not being in a form suitably stable to provide a commercially practical shelf life because of limited stability in an aqueous solution. Upon storage for extended periods, the therapeutic agents can degrade and become less potent. Accordingly, such devices have been generally impractical for use on outpatients and in doctor's offices, since the products do not have sufficient shelf life and neither the patient nor the practitioner wishes to wait the required time for the desired effect.

Several of the prior systems have attempted to overcome or minimize such limitations by adding the drug to the device prior to use or by maintaining the drug and/or electrode in a dry state prior to activation as disclosed, for example, in U.S. Pat. Nos. 4,722,726 (Sanderson et al.), 4,842,577 (Konno et al.), 4,911,707 (Heiber et al.), 4,917,676 (Heiber et al.), 5,087,242 (Pentelenz et al.), 5,158,537 (Haak et al.), 5,310,404 (Gyory et al.), and 5,385,543 (Haak et al.), the disclosures of which are hereby incorporated by reference in their entirety. However, limitations remain with respect to the use of such devices, particularly with respect to uniformity of hydration and consistency in the waiting time necessary for complete hydration and dilution of the drug formulation throughout the reservoir. The most significant problem associated with insufficient hydration being the uneven distribution of the current through the reservoir, resulting in "hot spots" or very localized area of high electrochemical activity. In severe situations, such hot spots may result in spiking of the current and burning of the patient.

Thus, there has been a need for an iontophoretic drug delivery system which would eliminate the problems and limitations associated with the prior devices discussed above, most significant of the problems being associated with determining when and if the patch is sufficiently hydrated and the drug formulation uniformly diluted so as to be able to apply the system to the patient to deliver the drug.

SUMMARY OF THE INVENTION

In contrast to the prior devices and systems discussed above, it has been found that a iontophoretic drug delivery system may be constructed in accordance with the present invention to prevent premature application of the system to the patient. In addition, the system of the present invention also indicates if the patch is not sufficiently hydrated for application to the patient. Also, the system can indicate if the patch is unsuitable for application.

The iontophoretic drug delivery system of the present invention includes a controller having a power source, a patch for attachment to the skin of a patient, the patch including electrode assembly, the electrode assembly including an electrode reservoir and a drug reservoir containing an active compound to be delivered to the patient, with the drug reservoir being hydratable, and means for monitoring the voltage drop across the surface of at least one of the reservoirs to determine the level of hydration of the reservoir.

In the preferred embodiment of the iontophoretic drug delivery system, the means includes a resistive network. Also, the resistive network includes a plurality of resistors arranged in an array. In addition, the resistive network includes a plurality of elongated resistors formed from an electrically conductive material. Further, the means includes a resistive network in the patch and means for measuring and calculating a voltage drop across the reservoir to determine a voltage signature.

The iontophoretic drug delivery system of the present invention includes a controller for providing a specific current to drive an ionizable substance into the skin of a patient, the controller, a patch removably, electrically coupled to the controller, the patch including an electrode assembly, the electrode assembly including an electrode reservoir and a drug reservoir containing an active compound to be delivered to the patient, with the drug reservoir being hydratable, and a resistive network coupled to at least one of the reservoirs, and means for monitoring a voltage of the resistive network and comparing the monitored voltage with a predetermined voltage signature so that the controller will permit current to flow for delivery of the drug only if the reservoirs are sufficiently hydrated.

In the preferred embodiment, the iontophoretic drug delivery system, the controller includes a microprocessor and the resistive network includes a resistive portion formed from an electrically conductive material.

The method for ensuring proper hydration of an iontophoretic patch of the present invention includes the steps of hydrating a reservoir containing a drug in a dry state, with the reservoir having a resistive network associated therewith, monitoring the voltage drop across the surface of the reservoir over time by measuring the voltage drop of each element in the resistive network, comparing the monitored voltage drop with a voltage signature to determine if the reservoir is sufficiently hydrated, and permitting current to flow from the controller to the patch if the monitored voltage drop is compatible with the voltage signature.

The preferred embodiment of the method for ensuring proper hydration of an iontophoretic patch also incudes the step of indicating the readiness of the patch to be applied to the skin of a patient.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

FIG. 2 is a schematic, cross-sectional side view of the patch illustrated in FIG. 1 prior to removal of the separating barrier and prior to attachment of the controller;

FIG. 3 is a schematic, cross-sectional side view of the patch and controller being removed from the supporting structure for attachment to the skin of a patient;

DETAILED DESCRIPTION OF THE PREFERRED EMBODIMENT

Figure 1A:
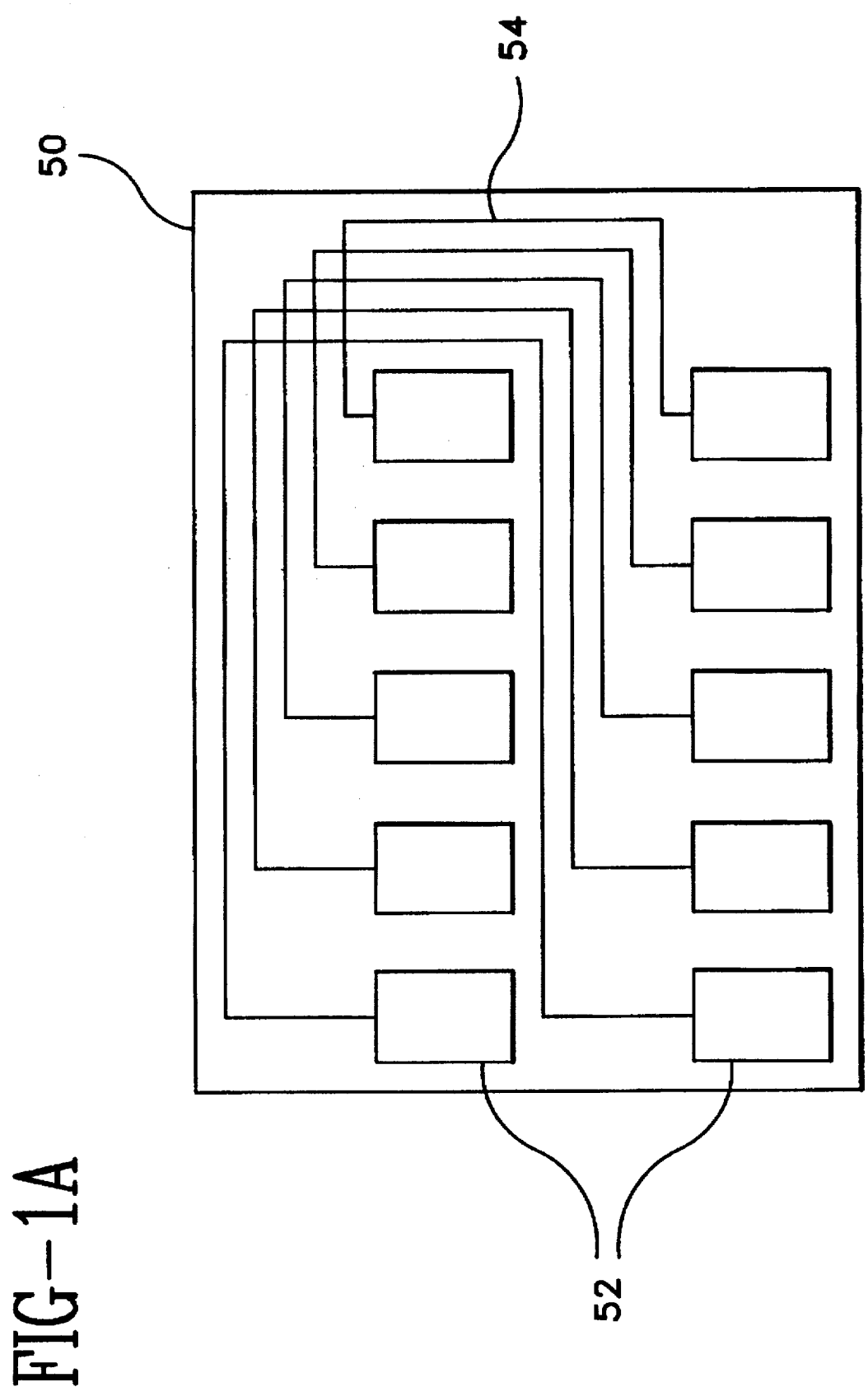
FIG. 1 is a schematic, cross-sectional side view of the patch and controller attached to one another to form the iontophoretic drug delivery system of the present invention, with FIG. 1A being an enlarged, fragmentary view of the patch illustrated in FIG. 1 showing the resistive network.

The iontophoretic drug delivery system of the present invention is illustrated in FIGS. 1–8 and generally includes the designation 10. Referring to FIG. 1, the device or system 10 of the present invention includes a patch 12 and a controller 14.

The patch 12 includes an electrode assembly 16, having at least one electrode, an electrode reservoir 18 and at least one drug reservoir 20, which are preferably held together by a suitable supporting structure 22. Preferably, the electrode is adhered to the electrode reservoir. It should be appreciated that a return electrode 16A may be combined in the electrode assembly 16 or separately provided.

As illustrated in FIGS. 1, 2 and 3, the supporting structure 22 is divided or otherwise separated into two portions 24, 26, one portion 24 (first) includes the electrode assembly 16 and the electrode reservoir 18 with the electrode reservoir being situated adjacent to the electrode assembly and holding an electrolyte. The other portion 26 (second) includes the drug reservoir 20 which holds the medication or drug 30 to be delivered iontophoretically. The two portions 24 and 26 are sealingly separated by a barrier 32 (FIG. 2). The barrier 32 includes an upper release liner 34 and a lower release liner 36 connected to one another by a pull tab 38 extending from the structure 22 (FIG. 2). The release surfaces are provided to prevent the barrier from adhering to the adjacent portions of the reservoirs 18, 20 and to seal the peripheral area surrounding each reservoir. In this way, the drug contained in the drug reservoir 20 can be stored or otherwise sealingly isolated from the electrode reservoir 18 in the first portion 24, in a dry state or formulation in a matrix or on a supporting substrate for hydration prior to use.

As illustrated in FIGS. 1, and in greater detail in FIG. 1A, a resistive network 50 is in contact with the drug reservoir 20 for monitoring the voltage at the surface of the reservoir. The resistive network 50 is at least partially fabricated from an electrically conductive material having a low impedance such as for example carbon, silver and the like. In the preferred embodiment, the network 50 includes a plurality of resistors 52 situated along electrical traces 54 interconnecting the resistors with the controller 12, which includes a source of electrical current 56. Preferably, the resistors 52 and traces 54 are printed or otherwise formed on a substrate as disclosed, for example, in patent application Ser. No. 08/012,168, now abandoned, entitled "ACTIVE DRUG DELIVERY DEVICE, ELECTRODE AND METHOD FOR MAKING SAME," the disclosure of which is hereby incorporated by reference in its entirety. In this way, the controller, among its other functions, may monitor the electrical voltage drop while current is allowed to pass through the reservoirs 18, 20 and the resistors 52, and if none is present, or a predetermined voltage signature is not detected over a predetermined period of time, the controller will not fully activate the patch for delivery of the drug. However, once the controller detects a voltage drop and the appropriate voltage signature, it preferably indicates readiness so that the patch 12 and controller 14 can be removed from the structure 22 for attachment to the skin of the patient (FIG. 3). In this way, it can be assured that the appropriate level of hydration of the reservoir is achieved.

Figure 6A:
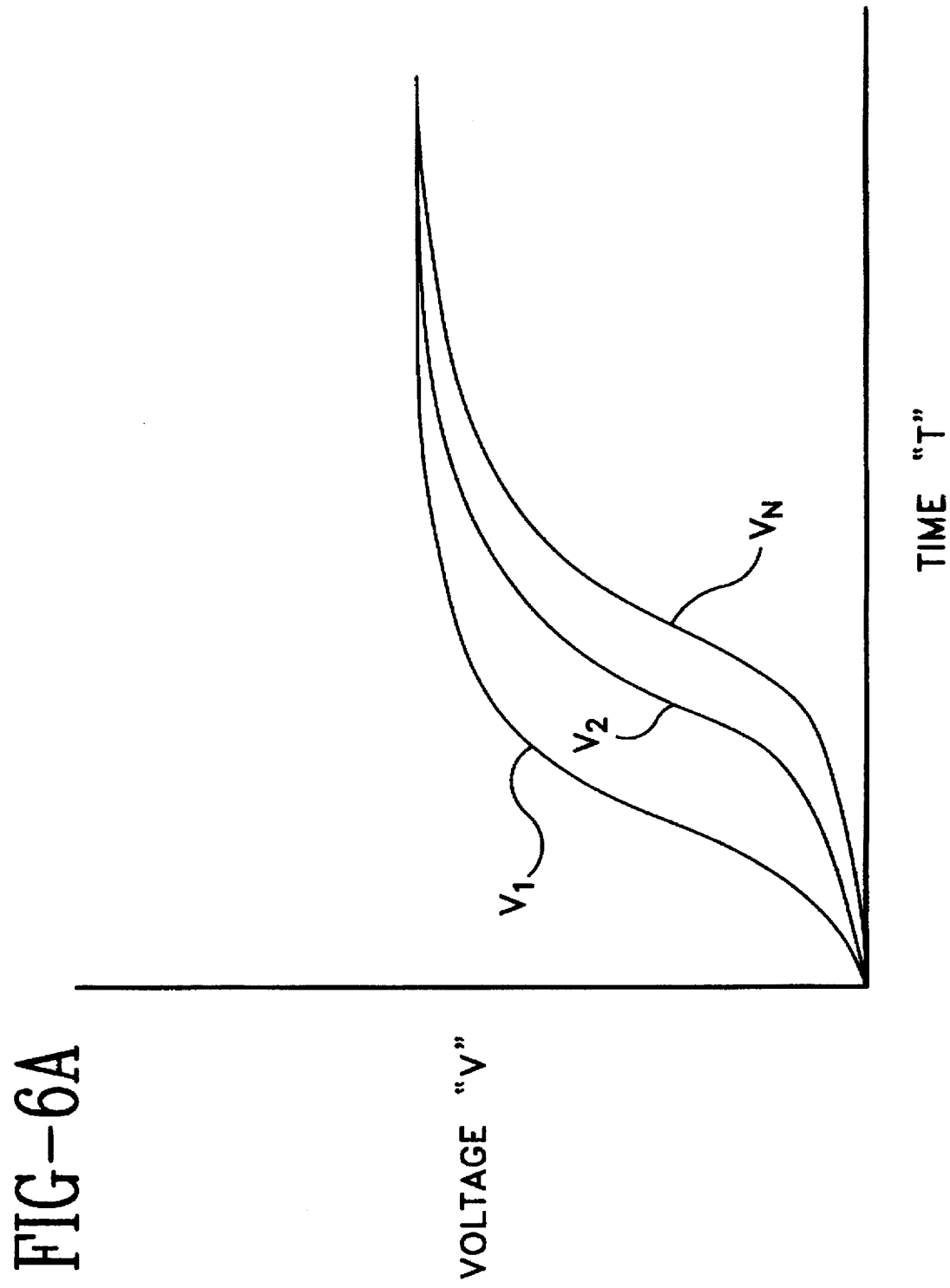
FIG. 6 is a schematic, cross sectional view of the iontophoretic drug delivery system of the present invention illustrated in FIG. 1 showing connection of another alternative embodiment of the resistive network to the circuitry for monitoring the voltage during hydration of the drug, with FIG. 6A being a graph showing an example of a voltage signature of the systems during monitoring.
Figure 7:
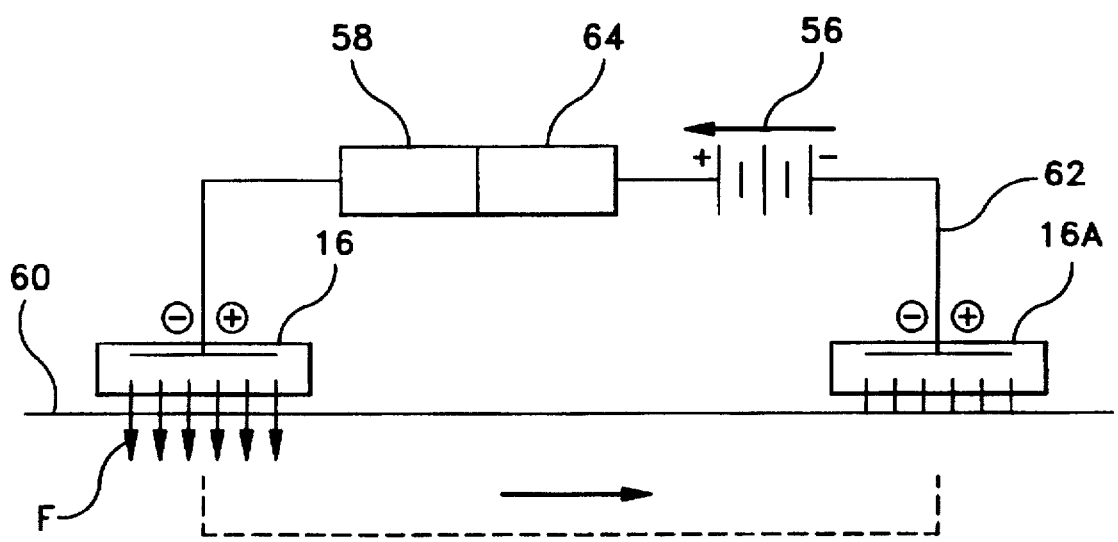
FIG. 7 is schematic, cross sectional view similar to FIGS. 4, 5 and 6 showing connection of the electrode assembly to the circuitry during delivery of the drug through the skin of the patient.

As illustrated in FIG. 1 and 3, and in greater detail in FIGS. 4, 5, 6 and 7, the controller 14 includes a power source 56 electrically connected to the electrode assembly 16 having one or more electrodes for establishing a uniform electric field for use in delivering the drug iontophoretically to an applied area of the patient 60 (FIG. 7).

Referring to FIGS. 3, 4, 5, 6 and 7, the controller 14 and the power source 56, such as for example a battery, are connected in a circuit, with the controller 14 preferably including a microprocessor 58, a dc/dc converter to increase the battery supply voltage, a current regulator which is controlled by the microprocessor and a switch 62 for switching the direction of the electrical current from a monitoring stage (FIGS. 4, 5 and 6) to a delivery stage (FIG. 7), and a timer 64 to provide the microprocessor 58 with a time base to monitor the voltage signature against during the monitoring state. In this way, if the proper voltage signature (FIGS. 4A, 5A, and 6A) is detected, the controller indicates that the system is ready to be applied to the skin of the patient.

In order to hydrate the patch, the barrier 32 is removed by pulling the tab 38 to remove the barrier 32, particularly the release liners 34, 36 from between the first and second portions 24, 26 (FIG. 2). In this way, upon manipulation, the electrode reservoir 18 and the drug reservoir 20 are brought into fluid conducting contact with one another and the drug may be dissolved at the interface of the reservoirs, due to its solubility in, for example, an aqueous fluid and/or the drug reservoir 18 is hydrated and adhered to the interface of the electrode reservoir. Thereafter, with the controller 14 attached to the patch 12, and the barrier removed, the controller monitors the voltage drop at the surface of the reservoir (FIGS. 4, 5 and 6).

Figure 4:
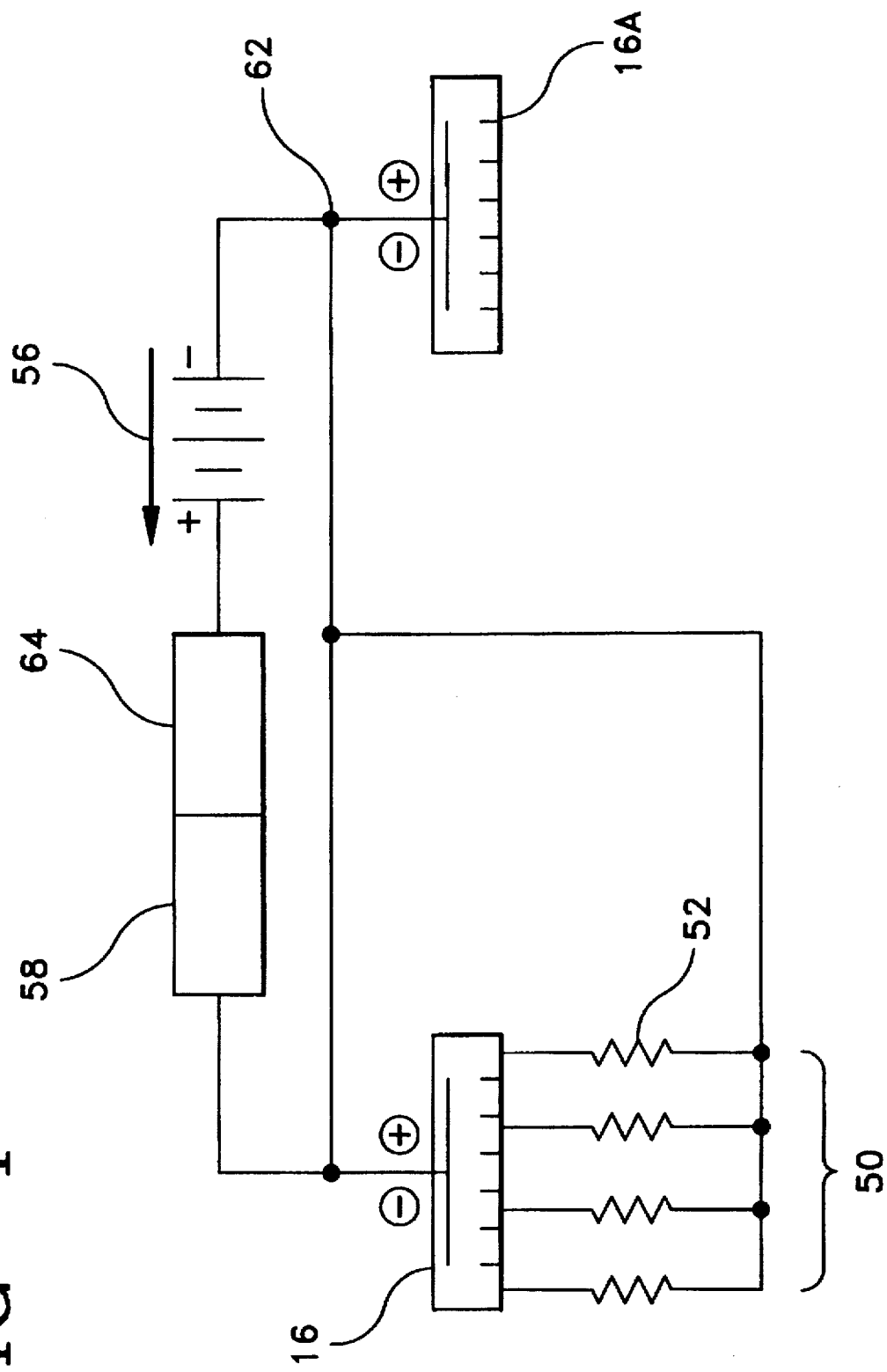
FIG. 4 is a schematic, cross sectional view of the iontophoretic drug delivery system of the present invention illustrated in FIG. 1 showing connection of the resistive network to the circuitry for monitoring the voltage during hydration of the drug, with FIG. 4A being a graph showing an example of a voltage signature of the systems during monitoring.

FIG. 4 illustrates the resistors 52 of the resistor network 50 including a voltage measuring device 65 for measuring the voltage such as, for example, a volt meter, differential voltage amplifier and the like. This voltage is monitored by the microprocessor and is the signal needed for the processor to make a determination of the hydration level of the reservoirs 18, 20. The graph illustrated in FIG. 4A shows a typical trace as a function of time for the voltage across the series combination of reservoir and resistor network. In this way, the voltage measuring device 65 will teach the microprocessor 58 of the change in the voltage shown in the graph.

Figure 5:
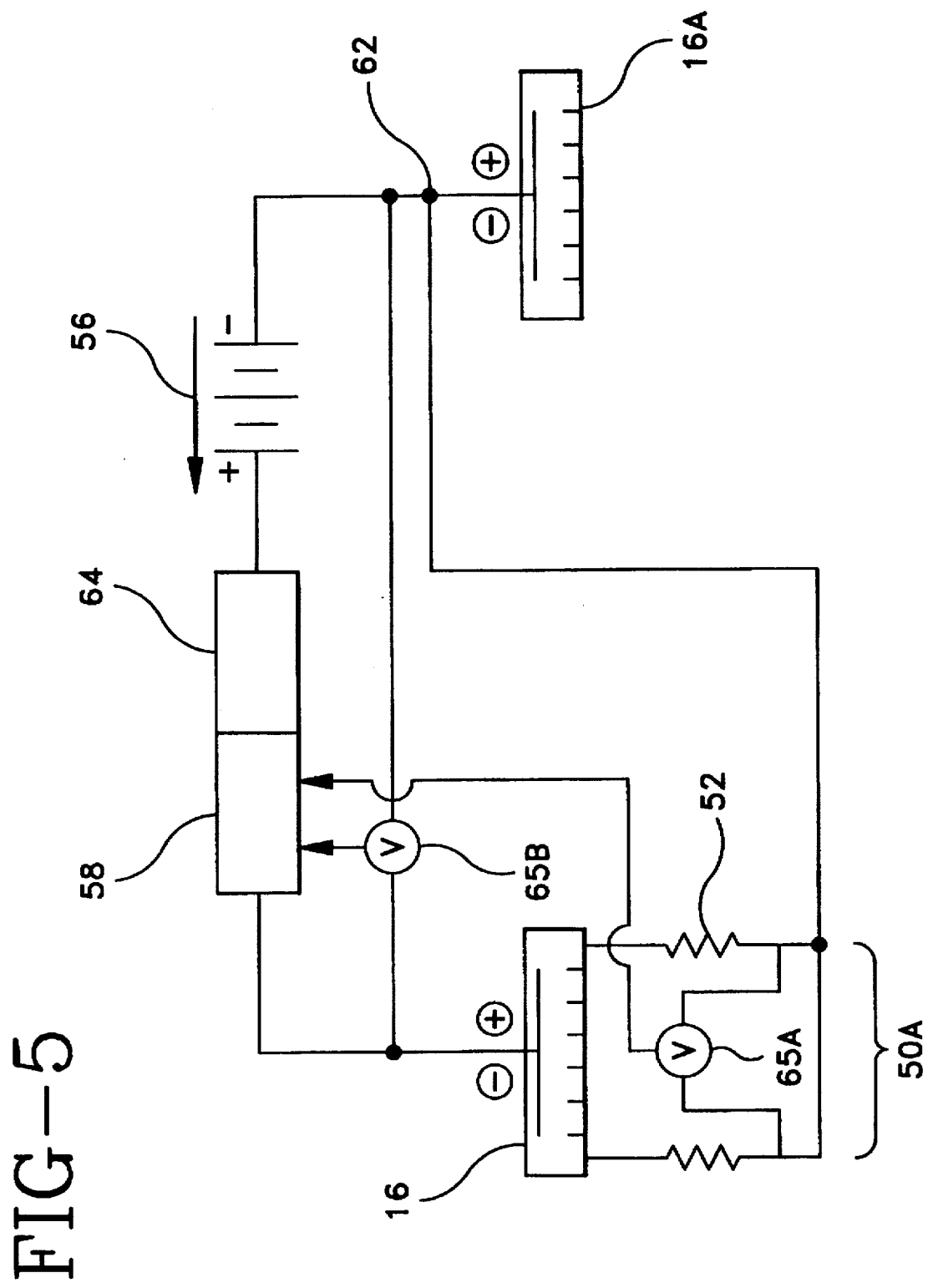
FIG. 5 is a schematic, cross sectional view of the iontophoretic drug delivery system of the present invention illustrated in FIG. 1 showing connection of an alternative embodiment of the resistive network to the circuitry for monitoring the voltage during hydration of the drug, with FIG. 5A being a graph showing an example of a voltage signature of the systems during monitoring.

FIG. 5 illustrates an alternative embodiment of the resistors 52 of the resistor network 50A using two different conductive contact points for measuring the resistance of the reservoir. These contact points, collectively, should cover the entire area of the reservoir, if during the process of passing current for making the measurement they accelerate the hydration process. The voltage measuring device 65A is placed between the two contact points as shown in FIG. 5, and makes the differential voltage available to the microprocessor in addition to the voltage measured by voltage measuring device 65B. To be acceptable, the voltage measured by device 65B must be below some minimum level and the differential voltage measured by device 65A must be near zero. It is unlikely that the two sample areas will have the same current passing unless they are equally hydrated.

Figure 5A:
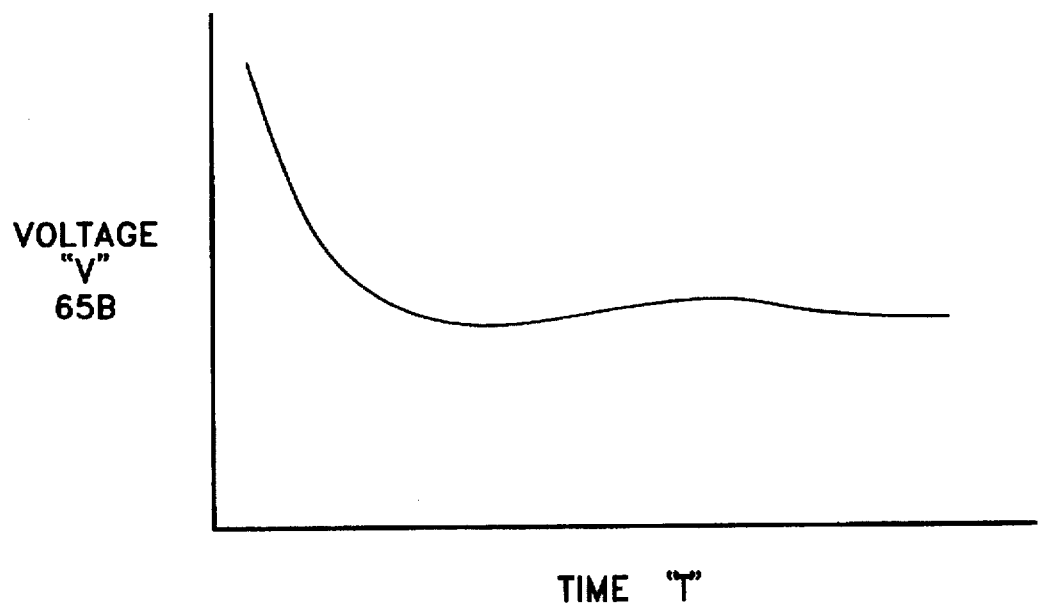
Figure 5B:
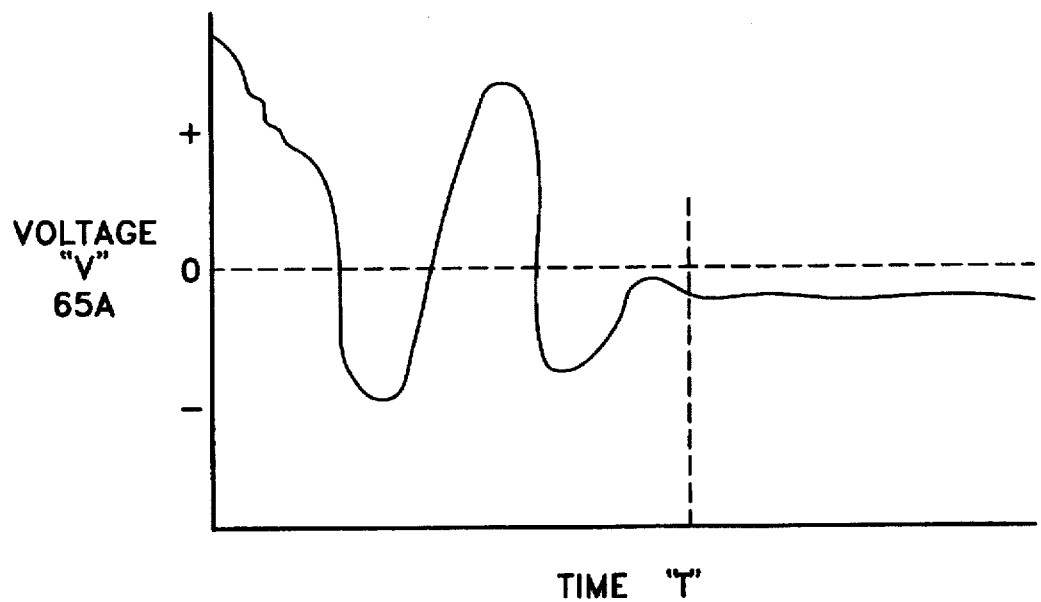

The graphs illustrated in FIG. 5A show typical voltage traces as a function of time at the monitoring points by device 65A, 65B for the corresponding resistor network 50A.

FIG. 6 illustrates another alternative embodiment of the resistors 52 of the resistor network 50B using an array of 1–n current paths, with the graph illustrated in FIG. 6A showing typical voltage traces as measured across the resistors giving a detailed mapping of the current distribution through the reservoirs 18, 20. In this way, the microprocessor will look for the current through each path to be equal.

To provide the user with the above information, the controller may include an indication device, such as an LED 68 (FIGS. 1 and 3), to visually indicate to the user whether the system is sufficiently hydrated so that it may be applied to the skin of the patient. The LED is electrically coupled to the microprocessor so that information received and stored by the microprocessor can be transmitted via the LED to a user, technician or health-care professional.

It should be appreciated to one skilled in the art that many factors, including, for example, the reservoir material, the drug to be delivered and the level of electrical current necessary to deliver the desired amount of drug during the desired application time, will determine the voltage signature. FIGS. 4A, 5A, and 6A show exemplary voltage signatures for a typical drug wherein the voltage will change during hydration until reaching a steady level. Thus, the controller can monitor the voltage level during the initial period for a steadily changing level and during the later period of time for a set period for a steady state.

Figure 8:
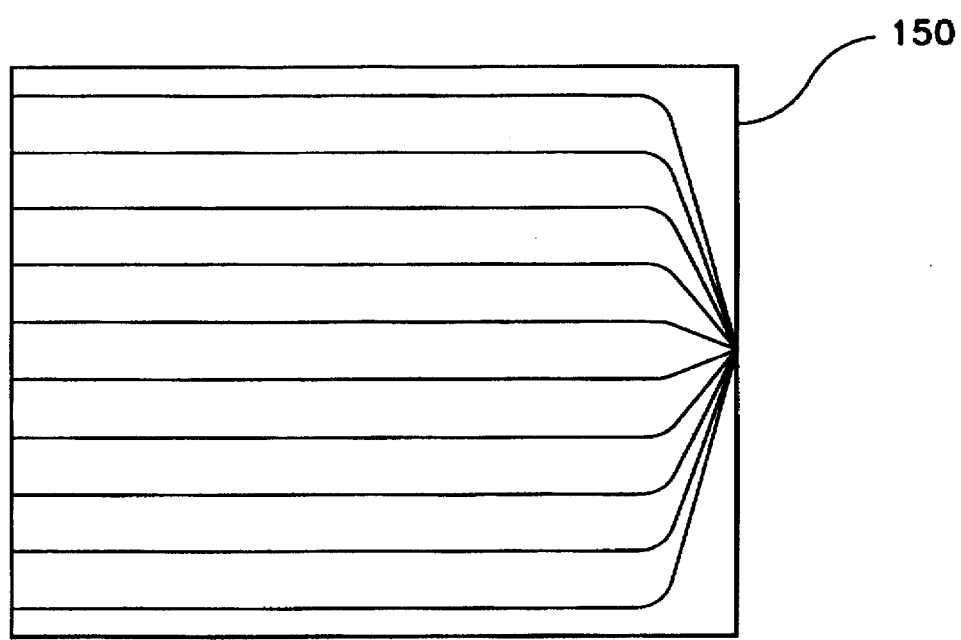
FIG. 8 is an enlarged, fragmentary view of an alternative embodiment of the resistive network illustrated in FIG. 1A.

Also, it should be appreciated that the resistive network 50 may be incorporated into a gel-reservoir to insure more intimate contact with the reservoirs 18, 20. In the alternative, the resistive network may be formed of a lamination 150 of conductive and non-conductive layers of elastomer as shown in FIG. 8. In addition, it should be appreciated that the resistive network may be sealingly attached to the patch 12 or the structure 22.

Active agent, drug, formulation, medication, medicament and active compound have been used herein to mean any pharmaceutical agent, such as therapeutic compounds, diagnostic agents, anesthetic agents and the like.

In addition, while the present invention has been described in connection with iontophoresis, it should be appreciated that it may be used in connection with other principles of active introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field. Also, it should be appreciated that the patient may include humans as well as animals. Further, while the present invention has been described in connection with the preferred system of the present invention, it should be appreciated that the method of the present invention may be utilized with other systems wherein it is necessary for the drug to be delivered and/or the reservoir to be maintained in a dry state prior to application to the skin of the patient, such as those described in U.S. Pat. Nos. 4,842,577 (Konno et al.), 4,911,707 (Heiber et al.), 4,917,676 (Heiber et al.), 5,087,242 (Pentelenz et al.), 5,158,537 (Haak et al.), 5,310,404 (Gyory et al.), and 5,385,543 (Haak et al.).

While the preferred embodiments of the present invention has been described so as to enable one skilled in the art to practice the system and method of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. An iontophoretic drug delivery system comprising:
   a controller having a power source;
   a patch for attachment to the skin of a patient, the patch including electrode assembly, said electrode assembly including an electrode reservoir and a drug reservoir containing an active compound to be delivered to the patient, with said drug reservoir being initially dehydrated;
   means for hydrating said drug reservoir; and
   means associated with the surface of at least one of the reservoirs for determining if the reservoir is sufficiently hydrated so that said controller permits current to flow for delivery of the drug if the reservoir is sufficiently hydrated and prevents current from flowing for delivery of the drug if the reservoir is insufficiently hydrated.

2. An iontophoretic drug delivery system as defined in claim 1, wherein the means includes a resistive network.

3. An iontophoretic drug delivery system as defined in claim 2, wherein said resistive network includes a plurality of resistors arranged in an array.

4. An iontophoretic drug delivery system as defined in claim 2, wherein said resistive network includes a plurality of elongated resistors formed from an electrically conductive material.

5. An iontophoretic drug delivery system as defined in claim 1, wherein the means includes a resistive network in said patch and means for measuring and calculating a voltage drop across said reservoir to determine a voltage signature.

6. An iontophoretic drug delivery system comprising:
   a controller for providing a specific current to drive an ionizable substance into the skin of a patient,
   a patch removably, electrically coupled to said controller, said patch including an electrode assembly, said electrode assembly including an electrode reservoir and a drug reservoir containing an active compound to be delivered to the patient, with said drug reservoir being hydratable, and a resistive network coupled to at least one of said reservoirs; and
   means for monitoring a voltage of the resistive network and comparing the monitored voltage with a predetermined voltage signature so that the controller will permit current to flow for delivery of the drug if the reservoirs are sufficiently hydrated and prevents current from flowing for delivery of the drug if the reservoirs are insufficiently hydrated.

7. An iontophoretic drug delivery system as defined in claim 6, wherein said controller includes a microprocessor.

8. An iontophoretic drug delivery system as defined in claim 6, wherein said resistive network comprises a resistive portion formed from an electrically conductive material.

9. A method for ensuring proper hydration of an iontophoretic patch comprising the steps of:
   hydrating a reservoir containing a drug in a dry state, with the reservoir having a resistive network associated therewith;
   monitoring the voltage drop across the surface of the reservoir over time by measuring the voltage drop of each element in the resistive network;
   comparing the monitored voltage drop with a voltage signature and determining if the reservoir is sufficiently hydrated; and
   permitting current to flow from said controller to said patch if the monitored voltage drop is compatible with the voltage signature.

10. The method for ensuring proper hydration of an iontophoretic patch defined in claim 9, further comprising the step of indicating the readiness of the patch to be applied to the skin of a patient.

* * * * *